United States Patent [19]
Dahlheim et al.

[11] Patent Number: 5,540,047
[45] Date of Patent: Jul. 30, 1996

[54] METHOD FOR REDUCING THE NITROGEN OXIDE CONCENTRATION IN THE EXHAUST OF AN INTERNAL COMBUSTION ENGINE OR OF A FIRING SYSTEM

[75] Inventors: Christian Dahlheim, Berlin; Maximilian Fleischer, Hoehenkirchen; Hans Meixner, Haar, all of Germany

[73] Assignee: Siemens Aktiengesellschaft, Munich, Germany

[21] Appl. No.: 319,290

[22] Filed: Oct. 6, 1994

[30] Foreign Application Priority Data

Oct. 6, 1993 [DE] Germany ............... 43 34 071.7

[51] Int. Cl.$^6$ .................................. F01N 3/20
[52] U.S. Cl. ................... 60/274; 60/276; 60/286
[58] Field of Search ............... 60/274, 276, 286

[56] References Cited

U.S. PATENT DOCUMENTS

| | | | |
|---|---|---|---|
| 4,751,054 | 6/1988 | Watanabe . | |
| 5,357,749 | 10/1994 | Ohsuga | 60/286 |
| 5,367,875 | 11/1994 | Aboujaoude | 60/286 |
| 5,369,956 | 12/1994 | Daudel | 60/286 |
| 5,410,873 | 5/1995 | Tashiro | 60/276 |

FOREIGN PATENT DOCUMENTS

| | | |
|---|---|---|
| 0362483 | 11/1990 | European Pat. Off. . |
| 3610364 | 1/1987 | Germany . |
| 3606535 | 3/1987 | Germany . |
| 4217552 | 8/1993 | Germany . |
| 53-129098 | 11/1978 | Japan . |
| 63-083652 | 4/1988 | Japan . |
| 4029049 | 1/1992 | Japan . |
| WO91/19975 | 12/1991 | WIPO . |

OTHER PUBLICATIONS

"Verhalten von SCR–Katalysatoren im dieselmotorischen Abgas", Dr.–Ing. Gerhard Lepperhoff and Dr.–Ing. Joachim Schommers, Motortechnische Zeitschrift 49 (1988) pp. 17–21.

"Untersuchung der $NO_x$–Reduzierung im Abgas von Dieselmotoren durch SCR–Katalysatoren", Dr–Ing. Gerhard Lepperhoff and Dr.–Ing. Georg Huethwohl, Motortechnische Zeitschrift 54 (1992) p. 310–315.

"Moeglichkeiten der Stickstoffoxidminderung Durch SCR–Anlagen", J. Becker, Grummersbach, Fachreport Rauchgasreinigung, Umwelt, 1986, No. 1, pp. 19–25.

"Sensors and Actuators", Letter to the Editors, Elsevier Sequoia/Printed in The Netherlands, (1989) pp. 259–265.

Sensors and Actuators, vol. 19, No. 3, Sep. 1989, Tatsumi Ishihara et al, "The Mixed Oxide $Al_2O_3$–$V_2O_5$ as a Semiconductor Gas Sensor for NO and $NO_2$", pp. 259–265.

*Primary Examiner*—Douglas Hart
*Attorney, Agent, or Firm*—Hill, Steadman & Simpson

[57] ABSTRACT

The method reduces the nitrogen oxide concentration in the exhaust of an internal combustion engine. A noticeable reduction in the $NO_x$ emission of a diesel motor can be achieved by applying the Selective Catalytic Reduction (SCR) method. In this method, ammonia is injected into a catalyzer through which the exhaust gas flows, this ammonia reacting with nitrogen monoxide or, respectively, nitrogen dioxide to form nitrogen and water. Since the exhaust gas should contain neither nitrogen monoxide nor excess ammonia, suitable methods are required for regulating the metering of $NH_3$. For controlling the amount of urea added to the exhaust gas as a reduction agent, the NO and $NH_3$ concentration is measured using a detector located in the exhaust systems following the SCR catalyzer. The detector contains a vanadate layer manufactured on the basis of a specific sputtering method as a sensitive element. The electrical resistance thereof is highest when the conversion of nitrogen monoxide to form nitrogen and water occurs stoichiometrically.

20 Claims, 9 Drawing Sheets

METHOD FOR REDUCING THE NITROGEN OXIDE CONCENTRATION IN THE EXHAUST OF AN INTERNAL COMBUSTION ENGINE OR OF A FIRING SYSTEM

BACKGROUND OF THE INVENTION

At the present time, the nitrogen oxide and particle emissions (dust) of a diesel motor optimized for power and consumption can only be insignificantly reduced on the basis of combustion-oriented measures. In order to be able to achieve the future exhaust limit values prescribed by legislators, an after-treatment is required of the exhaust gasses of diesel motors.

A noticeable reduction in the $NO_x$ emission of a diesel motor can be achieved by applying what is referred to as Selective Catalytic Reduction. In the SCR method, gaseous ammonia $NH_3$, ammonia in aqueous solution or urea is injected into the exhaust gas system as a reduction agent, so that the chemical reactions can occur at a catalyst. Approximately 0.9–1.1 mol $NH_3$ are required for reducing one mol $NO_x$ in the exhaust gas of the diesel motor. When less ammonia $NH_3$ is injected, the catalyst no longer works with the highest efficiency. An over-dosing is likewise to be avoided since unused ammonia $NH_3$ is emitted into the atmosphere.

The SCR method disclosed by German reference DE 36 10 364 can reduce the $NO_x$ part in the exhaust gas of firing systems by more than 80% and can simultaneously limit the $NH_3$ emission to less than 5 ppm. The dosing of the reduction agent is monitored by a computer that evaluates the output signal of a $NH_3$ sensor located in the exhaust system following the $NO_x$ converter and readjusts the delivery of reduction agent by driving a conveying unit as warranted. An electrochemical cell, that contains a cup-shaped body fabricated of stabilized zirconium dioxide as a critical component, serves as the $NH_3$ sensor. Two electrodes are applied to the solid electrolyte, whereby the outer electrode exposed to the exhaust gas is composed, for example, of $TiO_2$, $PtV_2O_5$ or $V_2O_5$ and the inner electrode exposed to a reference gas (air) is composed of platinum.

The method disclosed by German reference DE 36 06 635 for reducing the $NO_x$ concentration utilizes the high temperatures of the exhaust gas in order to evaporate the reduction agent present in solid or liquid form in order to split it into reactive components. Thereafter, the reactive components are injected via a bundle of pipelines into a comparatively cool zone of the exhaust system where they react with the nitrogen oxides to form nitrogen, water and carbon dioxide. A sensor working according to a chemiluminescence comparison method measures the $NO_x$ concentration. The output signal thereof is supplied to a regulator having a prescribed rated value that drives the motor of a dosing valve.

SUMMARY OF THE INVENTION

It is an object of the present invention to provide a method with which the concentration of nitrogen oxides $NO_x$ in the exhaust gas of an internal combustion engine or of a firing system can be noticeably reduced. In particular, it should be guaranteed that the exhaust gas contains neither nitrogen monoxide NO nor excess ammonia $NH_3$. This object is inventively achieved by a method for reducing the nitrogen oxide concentration in the exhaust of an internal combustion engine or of a firing system, whereby a reduction agent that contains ammonia is added to the exhaust and whereby nitrogen oxides are converted into nitrogen and water in a catalyzer unit through which the exhaust gas flows. A first sensor element that responds both to nitrogen monoxide as well as to ammonia is located in the exhaust system following the catalyzer unit. The electrical resistance or the electrical conductivity of the sensor element that is dependent on the nitrogen monoxide and ammonia concentration is measured. A quantity of reduction agent is added to the exhaust gas when the electrical resistance of the sensor element is highest or, respectively, when the electrical conductivity is lowest.

Gaseous ammonia, ammonia in aqueous solution or urea can be added to the exhaust gas as the reduction agent.

The electrical resistance or the electrical conductivity of a sensor element composed of a metal oxide/vanadate oxide mixture is measured. The sensor element can then be composed of an aluminum oxide/vanadium oxide mixture or of an iron oxide/vanadium oxide mixture.

The electrical resistance or the electrical conductivity of a sensor element composed of a vanadate $MeVo_4$ is measured, whereby Me is a trivalent metal. The sensor element can then be composed of aluminum or iron vanadate.

In one embodiment the sensor element is fashioned layer-like and is contacted by an electrode pair. In another embodiment the sensor element is actively heated and is kept at a constant temperature. In yet another embodiment a second sensor element corresponding to the first sensor element is arranged in the exhaust gas stream preceding the catalyzer unit and is utilized for measuring the nitrogen monoxide concentration.

The advantage that is achieved with the present invention is that the quantity of $NH_3$ required for an stoichiometric conversion of nitrogen monoxide NO into nitrogen $N_2$ and water $H_2O$ can be determined in a simple way by measuring the electroresistance of a vanadate layer exposed to the exhaust gas. An absolute measurement of the NO or, respectively, $NH_3$ concentration is not required. Since the control goal is a maximum resistance of the metal oxide layer employed as a sensor element, any resistance drift presents no problem.

BRIEF DESCRIPTION OF THE DRAWINGS

The features of the present invention which are believed to be novel, are set forth with particularity in the appended claims. The invention, together with further objects and advantages, may best be understood by reference to the following description taken in conjunction with the accompanying drawings, in the several Figures of which like reference numerals identify like elements, and in which:

DESCRIPTION OF THE PREFERRED EMBODIMENTS

Figure 1:
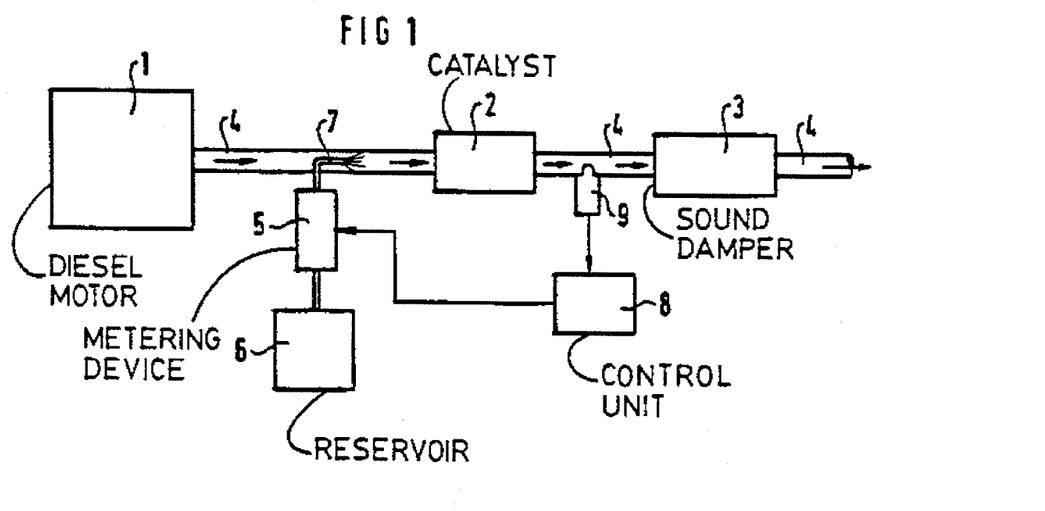
FIG. 1 depicts an exhaust system of a diesel motor equipped with a SCR catalyst.

The exhaust system of a diesel motor 1 schematically shown in FIG. 1 should largely decompose nitrogen oxides $NO_x$ arising during operation and output the remaining residual gasses to the atmosphere with as little noise as possible. It is composed, for example, of a SCR catalyst 2 (described in Motortechnische Zeitschrift 49 (1988) 1, pp. 17–21 and in Motortechnische Zeitschrift 54 (1993) 6, pp. 310–315), of one or more sound dampers 3 and of a pipe system 4 that connects the individual components to exhaust gas exit openings in the cylinder head of the diesel motor 1. A metering means 5 that injects the reduction agent stored in a reservoir 6 into the exhaust system precedes the SCR catalyst 2. The metering means 5, in particular, contains a membrane pump connected to an injection nozzle 7 or an injection valve having a preceding flow meter. A control unit 8 insures that a specific quantity of ammonia-containing reduction agent can be supplied to the exhaust gas.

An aqueous urea solution ($CO(NH_2)_2$) particularly comes into consideration as the reduction agent. This is decomposed upon application of heat to form carbon dioxide $CO_2$ and ammonia $NH_3$, whereby the ammonia $NH_3$ is adsorbed on the surface of the catalyst 2 and reacts with the nitrogen oxides NO and $NO_2$ in the exhaust gas to form the non-toxic substances of nitrogen $N_2$ and water $H_2O$. In order to assure that the diesel exhaust proceeding into the environment contains neither nitrogen monoxide NO nor excess ammonia $NH_3$, the reaction $$4NH_3+4NO+O_2 \rightarrow 4N_2+6H_2O$$

must occur stoichiometrically. The NO or, respectively, $NH_3$ concentration is therefore inventively measured using a detector 9 located in the exhaust pipe 4 following the SCR catalyst 2 and is utilized for controlling the injected quantity of urea. The quantity of urea required for a stoichiometric reaction is injected on the basis of the properties of the detector yet to be set forth when the electrical resistance of a vanadate layer employed as an element sensitive to NO or, respectively, $NH_3$ passes through a maximum or when the electrical conductively thereof passes through a minimum.

Figure 2:
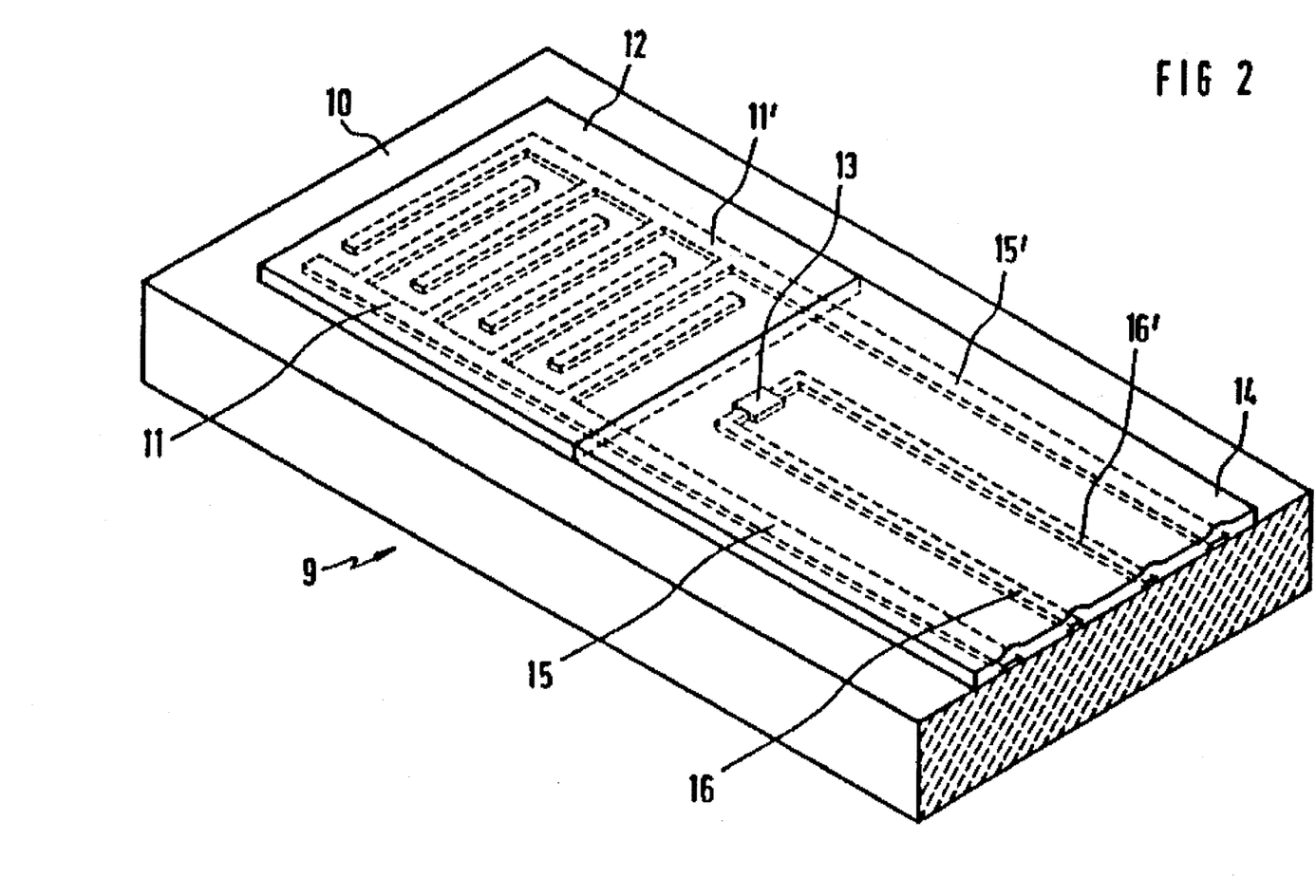
FIGS. 2 and 3 depict the schematic structure of a $NO/NH_3$ detector.
Figure 3:
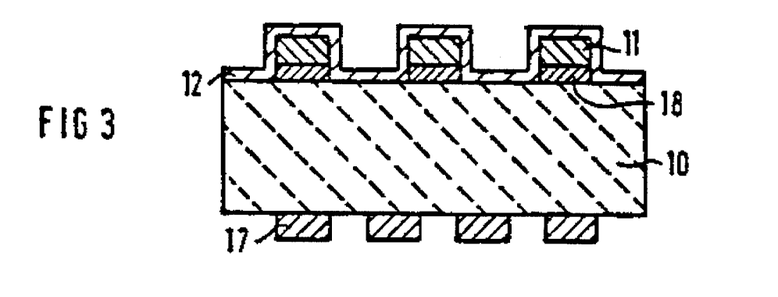

The substrate 10 of the detector 9 shown in FIGS. 1 and 2 is composed of an electrically insulating material such as glass, beryllium oxide BeO, aluminum oxide $Al_2O_3$ or silicon (with $Si_3N_4/SiO_2$ insulation). Two platinum electrodes 11, 11' forming an interdigital structure, a vanadate layer 12 ($AlVO_4$ or $FeVO_4$) that conductively connects these electrodes as a $NH_3$ or, respectively, NO-sensitive element, as well as a temperature sensor 13 are arranged on the substrate 10 that is between 0.1 and 2 mm thick. The passivation layer 14 of silicon oxide shields the lead 15, 15' or, respectively, 16, 16' respectively allocated to the two comb electrodes 11, 11' and to the temperature sensor 13 from the oxygen present in the exhaust gas.

In order to be able to set the desired operating temperature of up to 600° C. and in order to keep this constant independently of external influences, the detector 9 is actively heated by a resistance layer arranged on the backside of the substrate 10. The resistance layer referenced 17 in FIG. 2 is composed, for example, of platinum (Pt), gold (Au) or of an electrically conductive ceramic and has a meander-shaped structure. The metal layer 18 that is approximately 10–100 nm thick and is composed of titanium (Ti), chromium (Cr), nickel (Ni) or tungsten (W) and that improves the adhesion between the substrate 10 and the platinum electrodes 11, 11' is also shown.

The dimensions of the comb electrodes 11 and 11' are dependent on the specific resistance of the sensor layer 12 applied thereover in the desired temperature range. Thus, the comb structure 11, 11' can comprise thicknesses of, for example, 0.1–10 μm, widths of 1–1000 μm and electrode spacings of 1–100 μm. For a $AlVO_4$ layer 12 that is 1 μm thick, the following dimensions lead to well-measured, specific resistances in the temperature range between 500° and 600° C.:

electrode thickness D=1.5 μm, length of the interdigital structure L=1 mm, electrode spacing S=50 μm.

Figure 4:
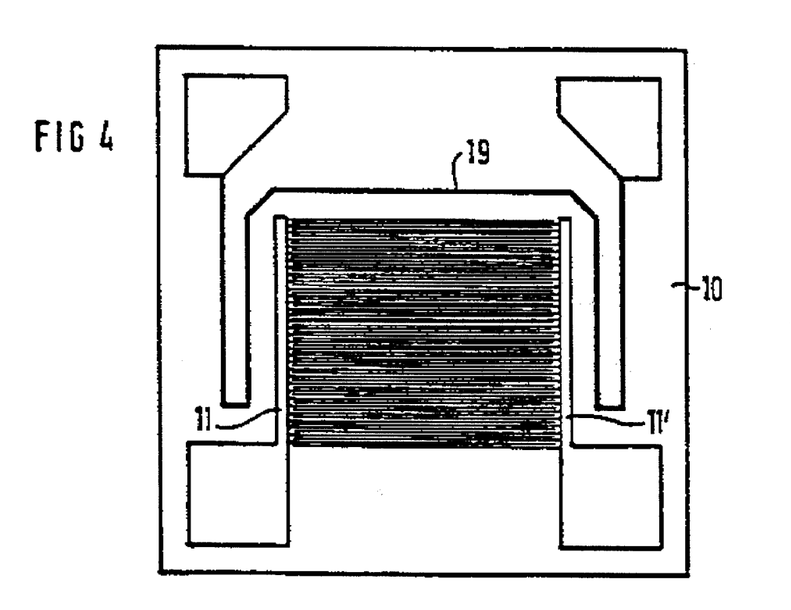
FIG. 4 depicts the comb electrodes of the $NO/NH_3$ detector.
Figure 5:
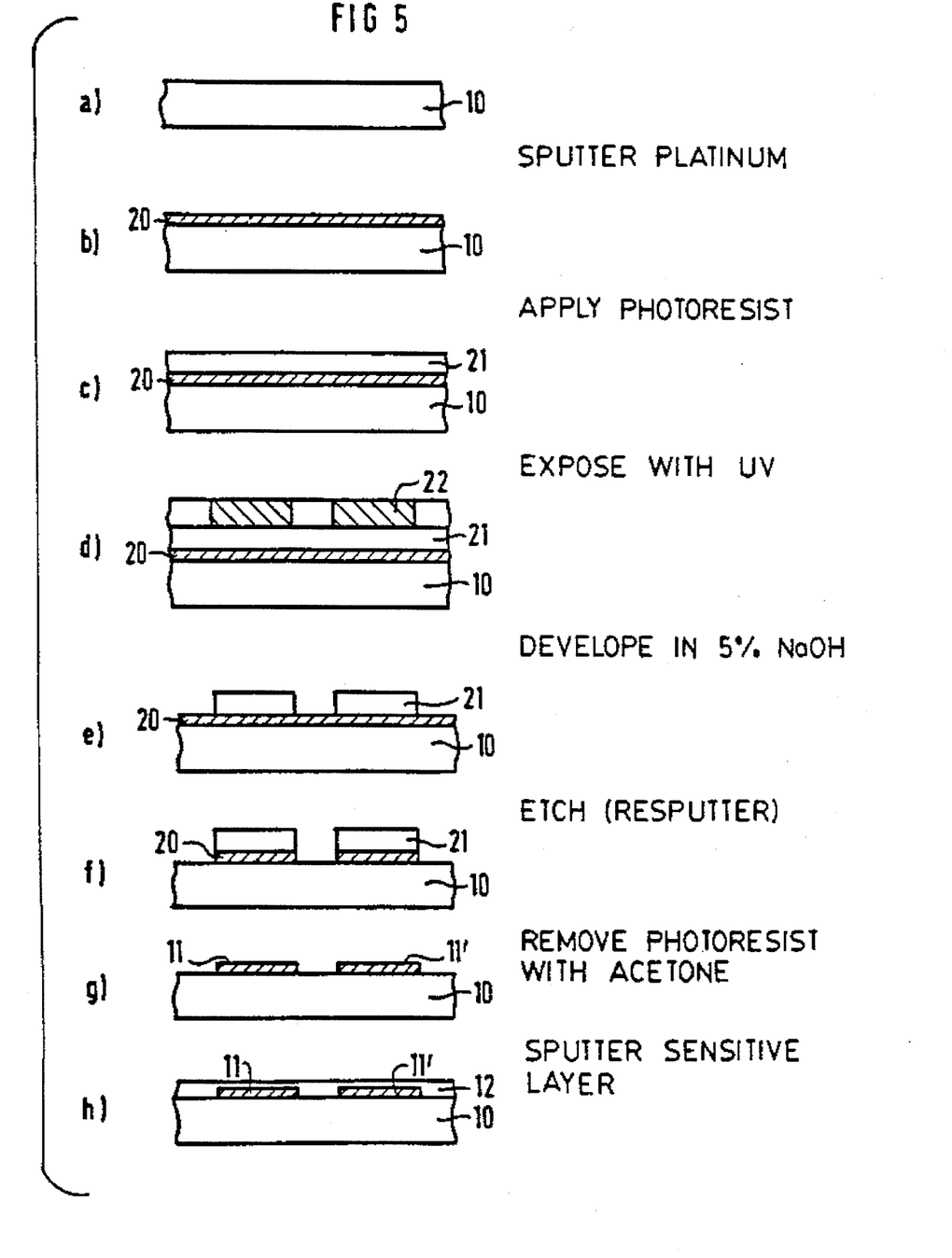
FIG. 5 depicts the method steps for manufacturing the comb electrodes.

FIG. 4 shows a true-to-scale illustration of an interdigital structure in plan view. A resistance layer 19 composed of platinum is employed in this exemplary embodiment as the temperature sensor. For manufacturing the comb electrodes 11, 11', a 1.5 μm thick platinum layer 20 is first deposited on the heated corundum substrate 10 in a sputtering system (see FIGS. 5a, b). The structuring of the layer 20 ensues in a positive photo step wherein the photoresist 21 is applied at the location of the electrodes to be produced and is exposed through a mask 22 (see FIGS. 5c, d, e). The developed photoresist 21 protects the platinum layer 20 during the following etching step (see FIG. 5f). After the removal of the photoresist 21 with acetone, the desired comb electrodes 11 and 11' (see FIG. 5g) on which the gas-sensitive vanadate layer 12 is subsequently deposited (see FIG. 5h) is obtained.

The employment of gold Au instead of platinum Pt as an electrode material has no influence on the gas sensitivity of the mixed oxide $Al_2O_3/V_2O_5$.

Figure 6:
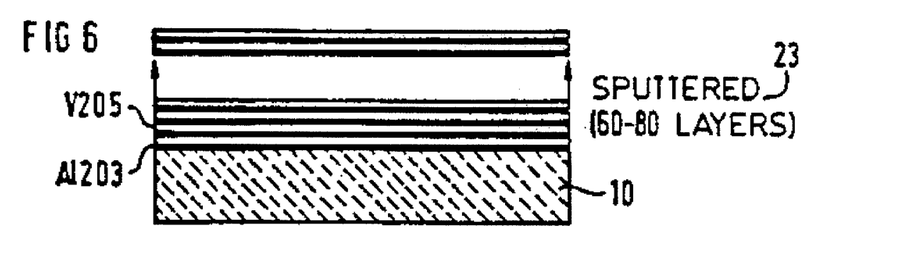
FIG. 6 depicts a $Al_2O_3$-$V_2O_5$ sandwich structure deposited on the comb electrodes.

The extraordinary properties of the detector are based on the sputtering method to be employed in the manufacture of the gas-sensitive layer 12 and on the tempering following thereupon. The coating of the comb electrodes 11, 11' can be undertaken, for example, in the sputtering system Z490 manufactured by Leybold. Metallic vanadium (V) and aluminum (Al) serve as initial materials, these being reactively triturated from the corresponding targets in a plasma composed of 80% argon and 20% oxygen and precipitating on the heated substrate 10. As a result of alternating trituration of the two targets, the sandwich structure 23 shown in FIG. 6 arises. It has a thickness of approximately 1 μm and is respectively composed of 60–80 $V_2O_5$ or, respectively, $Al_2O_3$ layers that are approximately 10–15 nm thick, whereby the $Al_2O_3$ part amounts to between 50% through a maximum of 70%. The sputtering parameters are as follows:

Residual gas pressure ca.=$2-4\times10^{-6}$ mbar;

Sputtering gas pressure=$4.2\times10^{-3}$ mbar;

Sputtering gas=20% $O_2$/80% Ar;

DC potential=Al-Target: 155 V, V-Target: 225 V; and

Substrate temperature=ca. 250° C.

In order to produce a uniform mixed oxide, the sandwiched structure 23 is tempered in a high-temperature furnace in air for approximately 5–15 hours. The furnace temperature thereby has a critical influence on the topography and on the phase of the $Al_2O_3/V_2O_5$ layers. An optimum sensitivity for ammonia $NH_3$ and nitrogen monoxide NO is exhibited by layers that were tempered at temperatures T between $550°\ C.\leq T\leq 610°\ C.$ and are composed of equal parts $V_2O_5$ and $Al_2O_3$. As a result of the tempering, the aluminum vanadate $AlVO_4$ responsible for the high gas sensitivity arises. The maximum working temperature of the vanadate layer lies at approximately 600° C. Aluminum vanadate $AlVO_4$ has a triclinic unit cell with a=0.6471 nm, b=0.7742 mn, c=0.9084 nm, $\alpha$=96.848A, $\beta$=105,825A and $\chi$=101,399A. A volume V thereof amounts to V=0.4219 $nm^3$.

Layers having an $Al_2O_3$ part of more than 50% exhibit a somewhat lower measuring effect. However, they can also be utilized at higher temperatures of up to 680° C.

The following diagrams are intended to document the sensitivity of the $AlVO_4$ thin-films manufactured according to the disclosed method to various gasses. The quantity $\sigma/\sigma_o$ ($\sigma_o$=the conductivity of the sensitive layer in synthetic air (80% $N_2$/20% $O_2$)) is respectively entered dependent on the time T or, respectively, on the concentration of the respective gas.

Figure 7:
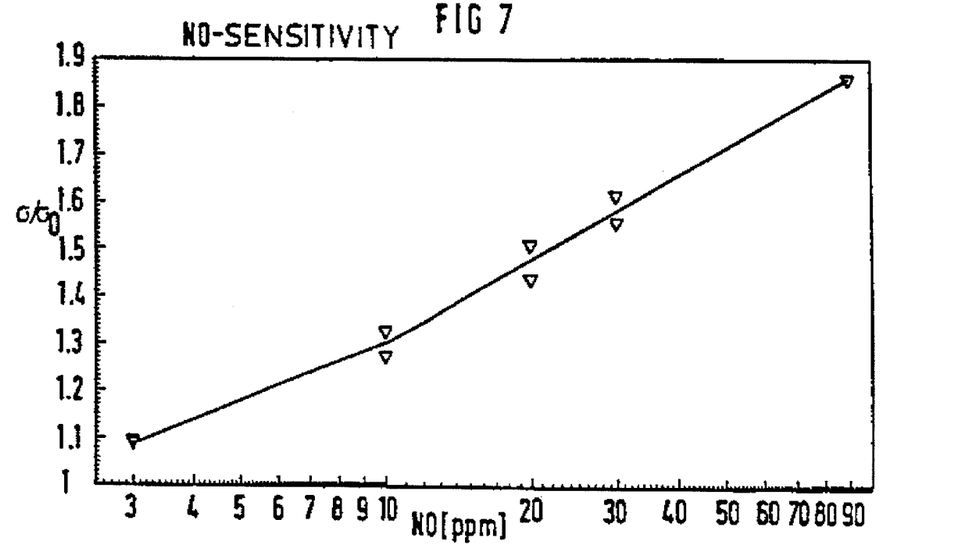
FIGS. 7–11 depict the sensitivity of a $AlSo_4$ thin-film to nitrogen monoxide NO, ammonia $NH_3$ and other gasses.
Figure 8:
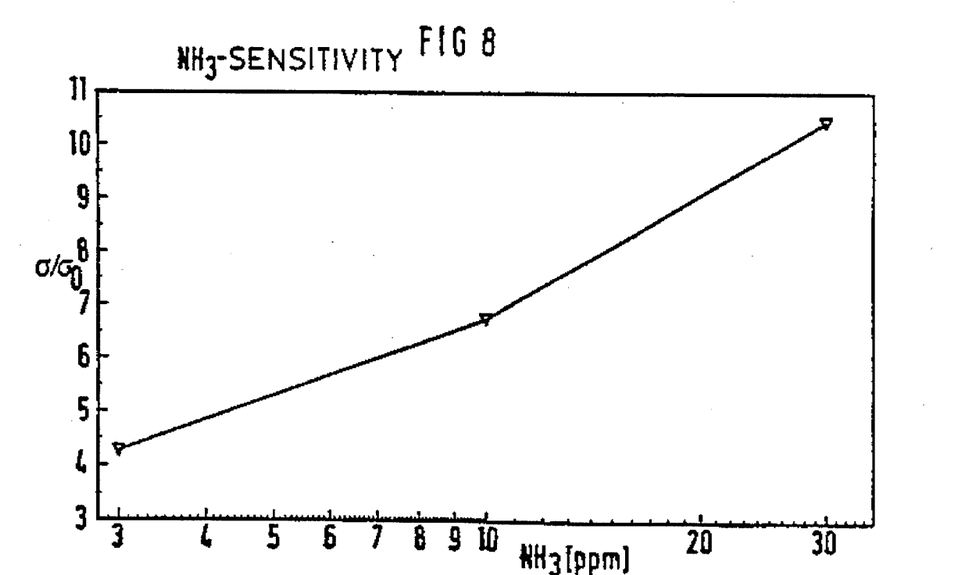

The presence of even the minutest quantities of nitrogen monoxide NO and ammonia $NH_3$ in dry, synthetic air leads to a noticeable rise in the conductivity of the aluminum vanadate $AlVO_4$ (see FIGS. 7 and 8). The conductivity thus changes by approximately 75% when 10 ppm nitrogen monoxide NO are added to the air. The addition of 10 ppm ammonia $NH_3$ results in an increase of the conductivity by more than a factor of 6.

Figure 9:
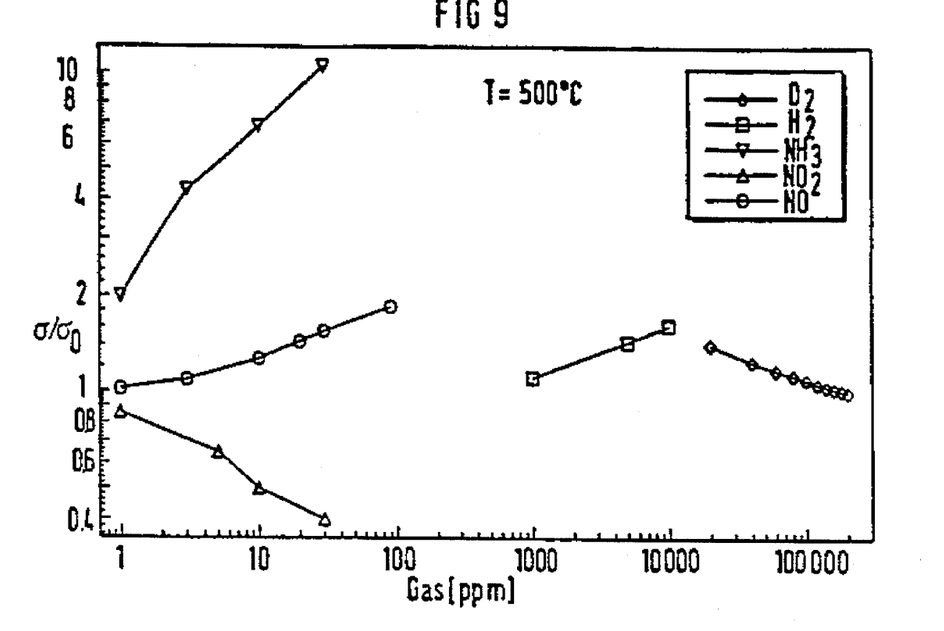

As FIG. 9 shows, the specific resistance of the $AlVO_4$ thin film increases given the presence of nitrogen dioxide $NO_2$. Since the aluminum vanadate exhibits completely different behavior relative to nitrogen monoxide NO (reduction of the specific resistance, see FIG. 7), the two nitrogen oxides can be clearly distinguished from one another insofar as only one of the two nitrogen oxides interacts with the sensitive element.

Figure 10:
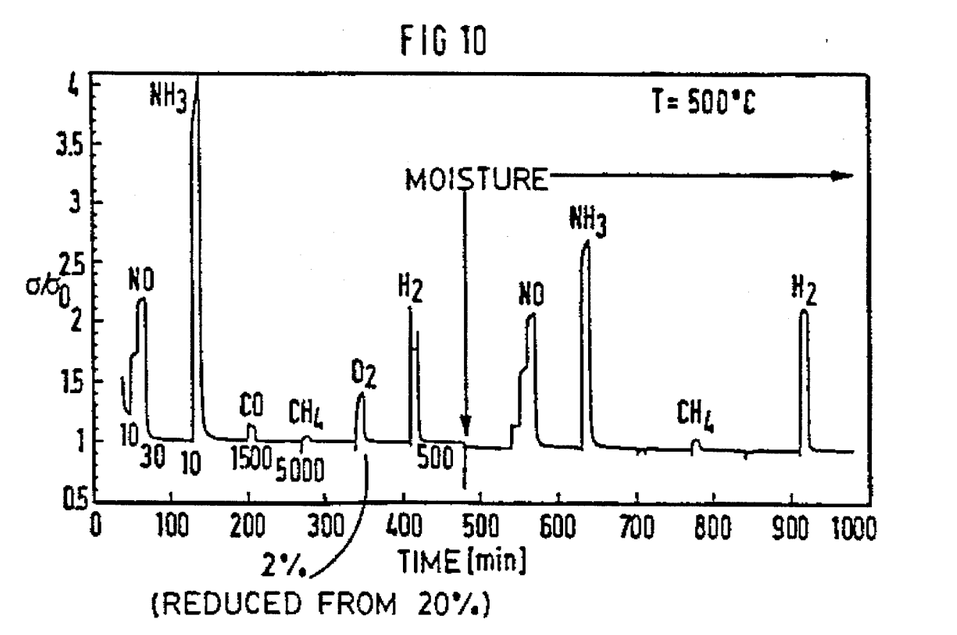

In addition to responding to nitrogen monoxide NO and ammonia $NH_3$, the vanadate layer also responds to changes in the partial oxygen pressure and hydrogen $H_2$ (see FIG. 10). The cross sensitivity to oxygen $O_2$ and hydrogen $H_2$, however, is substantially lower than the reaction to nitrogen monoxide NO and ammonia $NH_3$. Thus, 500 ppm hydrogen $H_2$ in air result in approximately the same modification of the conductivity as the addition of 10 ppm nitrogen monoxide NO. The gasses carbon monoxide CO (up to 1500 ppm), methane $CH_4$ (up to 5000 ppm) and carbon dioxide $CO_2$ (up to 1%) cannot be documented up to the respective concentration recited in parentheses. In a moist gas mixture (80 mbar $H_2O$), a noticeable decrease in the $NH_3$ sensitivity is observed; however, it still remains twice as great as the sensitivity for nitrogen monoxide NO (see the right-hand part of FIG. 9).

Figure 11:
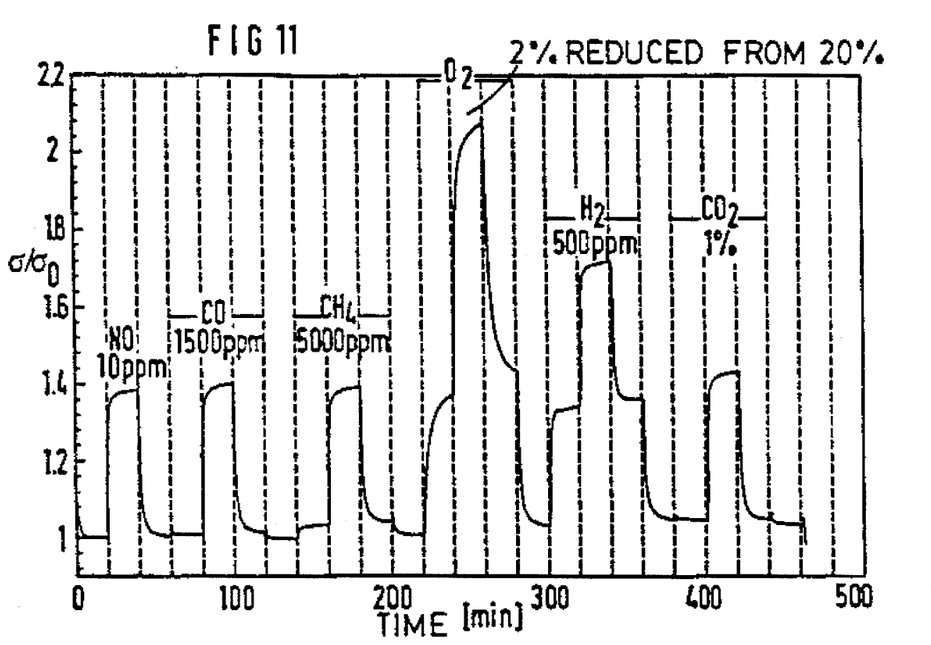
Figure 12A:
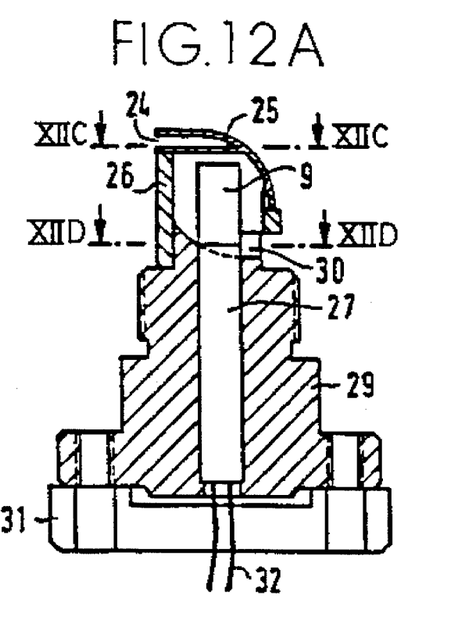
FIG. 12 depicts an exemplary embodiment of a detector housing.
Figure 12B:
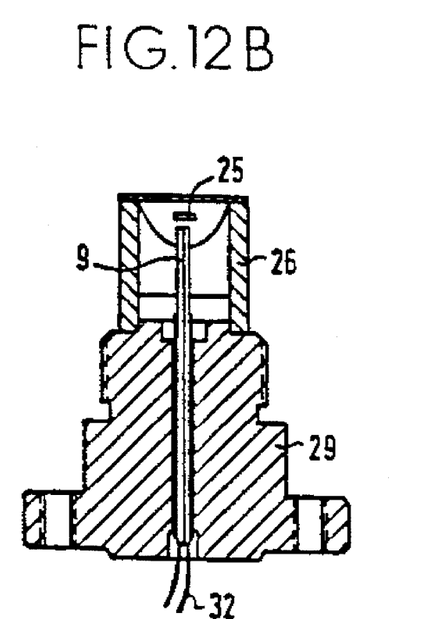
Figure 12C:
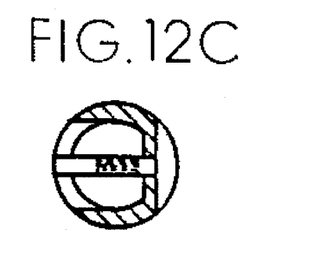
Figure 12D:
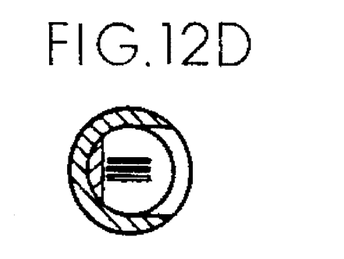

FIG. 11 shows the sensitivity of the $AlVO_4$ thin film in moist air (80 mbar $H_2O$) at 500° C. and a NO part of 10 ppm. A further gas in the recited concentration was added to the moist air within the time intervals respectively marked by a horizonal line. The air between, for example, the 60th and the 120th minute thus contained 1500 ppm carbon monoxide CO and additionally contained 10 ppm nitrogen monoxide NO between the 80th and the 100th minute. As the measured results show, the NO sensitivity of the $AlVO_4$ layer is not influenced by the presence of carbon monoxide CO, methane $CH_4$ and carbon dioxide $CO_2$. The mixture of hydrogen $H_2$ in fact does not effect a masking of the NO sensitivity but a clear cross sensitivity is found. A similar effect is observed given oxygen $O_2$ when the concentration thereof is reduced from 20% to 2%.

The stainless steel housing shown in FIG. 12 serves the purpose of incorporating the detector 9 into the wall of the exhaust pipe 4. The housing is composed of two parts, whereby the housing head 26 having a gas entry opening 24 and a metal web 25 is secured on the base member 29 that is provided with a bore 27 for the acceptance of the detector 9. Before the two parts 26 and 29 are welded, the detector 9 is glued in the bore 27 of the base member 29. After assembly, the sensitive element is located in an S-shaped flow channel that connects the gas entry opening 24 to the gas exit opening 30. In the left-hand part of FIG. 12, the ceramic plate 31 that terminates the bore 27 of the lower housing part 29 is also shown. It contains a plurality of channels through which the leads 32 serving the purpose of contacting the detector 9 are conducted to the outside.

Figure 13:
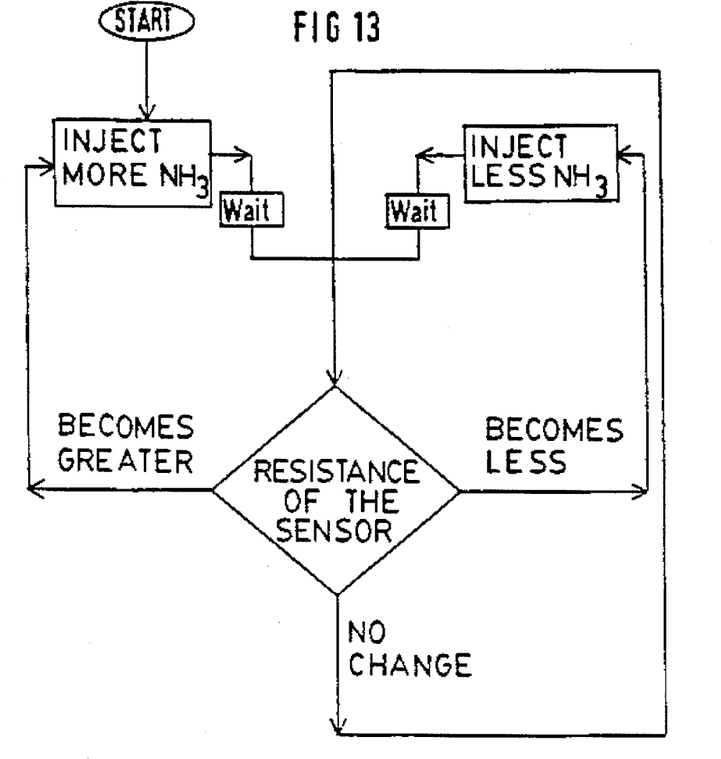
FIG. 13 is a flow chart that explains the method for regulating the quantity of urea injected.

A simple and effective method for regulating the urea injection into the SCR catalyst 2 can be realized using the above-described $NO/NH_3$ detector 9. Since the detector 9 reacts with an increase in the conductivity both with respect to nitrogen monoxide NO as well as with respect to ammonia $NH_3$ (see FIGS. 7 and 8), one can initially not decide which of the two gases is interacting with the sensitive layer 12. As may be seen with reference to the flow chart shown in FIG. 13, the control unit 8 will cause the metering means 5 to initially inject more urea into the exhaust gas. When this measure leads to an increase in the sensor resistance, then the nitrogen monoxide NO cannot yet have been completely converted into nitrogen $N_2$ and water $H_2O$. The injected quantity of urea is then increased until the sensor resistance reaches the maximum value indicated by an arrow in FIG. 14 and the exhaust gas leaving the catalyst 2 contains neither nitrogen monoxide NO nor excess ammonia $NH_3$.

Figure 14:
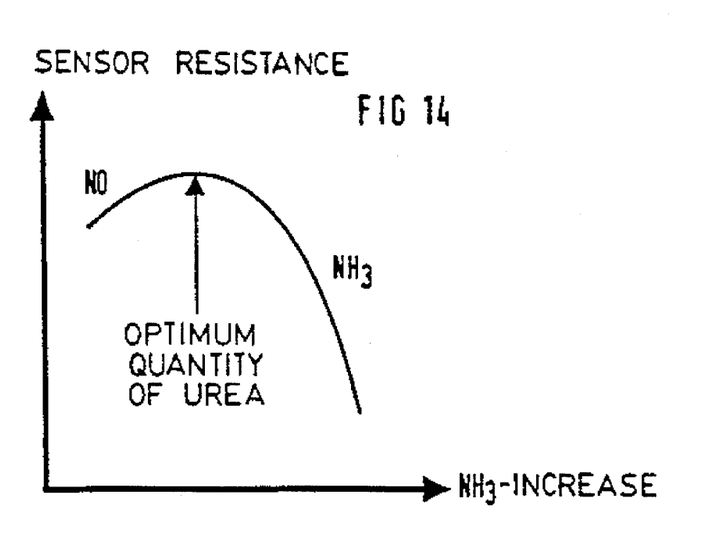
FIG. 14 shows the electrical resistance of a vanadate layer in a gas mixture containing nitrogen monoxide NO and ammonia $NH_3$ dependent on the quantity of ammonia $NH_3$ added to the gas mixture.

When, by contrast, the increased injection of urea leads to a lower sensor resistance, the $NH_3$ excess in the exhaust gas must be decomposed by reducing the quantity of urea (see the right-hand part of the flow chart). In the diagram of FIG. 14, the maximum value of the sensor resistance that defines the optimum quantity of urea is therefore approached from the right.

The invention, of course, is not limited to the exemplary embodiments that have been set forth. Thus, for example, it is possible to arrange a second detector on the basis of sputtered $Al_2O_3/V_2O_5$ layers in the exhaust system preceding the injection nozzle 7. This second detector then mainly serves the purpose of monitoring the described control, in that the NO concentration is measured and is compared to the quantity of urea that is respectively injected. The $NH_3$ sensitivity of the detector thereby does not have a disturbing effect since the motor exhaust contains no ammonia $NH_3$ preceding the injection nozzle 7.

Instead of urea, ammonia in an aqueous solution or gaseous ammonia also can be used as a reduction agent, whereby the reduction agent can also be directly injected into the SCR catalyst 2.

The method of the present invention, of course, can also be employed in what are referred to as $DeNO_x$ systems for removing nitrogen from flue gases (see, for example, Umwelt, 1986 No. 1, Fachreport Rauchgasreinigung, FR 19-25).

The invention is not limited to the particular details of the method depicted and other modifications and applications are contemplated. Certain other changes may be made in the above described method without departing from the true spirit and scope of the invention herein involved. It is intended, therefore, that the subject matter in the above depiction shall be interpreted as illustrative and not in a limiting sense.

What is claimed is:

1. A method for reducing nitrogen oxide concentration in exhaust gas in an exhaust system of an internal combustion engine or of a firing system, a reduction agent that contains ammonia being added to the exhaust gas and nitrogen oxides being converted into nitrogen and water in a catalyzer unit in the exhaust system through which the exhaust gas flows, comprising the steps of:

provinding a first sensor element that responds both to nitrogen monoxide and to ammonia in the exhaust system following the catalyzer unit;

measuring electrical resistance or electrical conductivity of the sensor element, the electrical resistance or electrical conductivity being dependent on the nitrogen monoxide and ammonia concentration; and adding a quantity of reduction agent to the exhaust gas when the electrical resistance of the sensor element is highest or, respectively, when the electrical conductivity is lowest.

2. The method according to claim 1, wherein gaseous ammonia, ammonia in aqueous solution or urea is added to the exhaust gas as the reduction agent.

3. The method according to claim 1, wherein a sensor element composed of a metal oxide/vanadium oxide mixture is provided.

4. The method according to claim 3, wherein a sensor element composed of an aluminum oxide/vanadium oxide mixture or of an iron oxide/vanadium oxide mixture is provided.

5. The method according to claim 1, wherein a sensor element composed of a vanadate $MeVO_4$ is provided, where Me is a trivalent metal.

6. The method according to claim 5, wherein a sensor element composed of aluminum or iron vanadate is provided.

7. The method according to claim 1, wherein a sensor element that is fashioned layer-like and that is contacted by an electrode pair is provided.

8. The method according to claim 1, wherein the method further comprises actively heating the sensor element and keeping the sensor element at a constant temperature.

9. The method according to claim 1, wherein the method further comprises providing a second sensor element, corresponding to the first sensor element, in the exhaust gas system preceding the catalyzer unit and using the second sensor element for measuring nitrogen monoxide concentration in the exhaust gas.

10. A method for reducing nitrogen oxide concentration in exhaust gas in an exhaust system of an internal combustion engine or of a firing system, the exhaust system having a catalyzer unit through which the exhaust gas flows, comprising the steps of:

providing a reduction agent composed of one of gaseous ammonia, ammonia in an aqueous solution, and urea;

providing a first sensor element that responds both to nitrogen monoxide and to ammonia in the exhaust system following the catalyzer unit;

measuring electrical resistance or electrical conductivity of the sensor element, the electrical resistance or electrical conductivity being dependent on the nitrogen monoxide and ammonia concentration; and adding a quantity of reduction agent to the exhaust gas when the electrical resistance of the sensor element is highest or, respectively, when the electrical conductivity is lowest such that the nitrogen oxides in the exhaust gas are converted into nitrogen and water in the catalyzer unit.

11. The method according to claim 10, wherein a sensor element composed of a metal oxide/vanadium oxide mixture is provided.

12. The method according to claim 10, wherein a sensor element composed of a vanadate $MeVO_4$ is provided, where Me is a trivalent metal.

13. The method according to claim 10, wherein a sensor element that is fashioned layer-like and that is contacted by an electrode pair is provided.

14. The method according to claim 10, wherein the method further comprises actively heating the sensor element and keeping the sensor element at a constant temperature.

15. The method according to claim 10, wherein the method further comprises providing a second sensor element, corresponding to the first sensor element, in the exhaust gas system preceding the catalyzer unit and using the second sensor element for measuring nitrogen monoxide concentration in the exhaust gas.

16. A method for reducing nitrogen oxide concentration in exhaust gas in an exhaust system of an internal combustion engine or of a firing system, the exhaust system having a catalyzer unit through which the exhaust gas flows, comprising the steps of:

providing a reduction agent composed of one of gaseous ammonia, ammonia in an aqueous solution, and urea;

providing at least one sensor element that responds both to nitrogen monoxide and to ammonia in the exhaust system following the catalyzer unit, the first sensor element being composed of a metal oxide/vanadium oxide mixture;

measuring electrical resistance or electrical conductivity of the sensor element, the electrical resistance or electrical conductivity being dependent on the nitrogen monoxide and ammonia concentration; and adding a quantity of the reduction agent to the exhaust gas when the electrical resistance of the sensor element is highest or, respectively, when the electrical conductivity is lowest such that the nitrogen oxides in the exhaust gas are converted into nitrogen and water in the catalyzer unit.

17. The method according to claim 16, wherein a sensor element composed of an aluminum oxide/vanadium oxide mixture or of an iron oxide/vanadium oxide mixture is provided.

18. The method according to claim 16, wherein a sensor element that is fashioned layer-like and that is contacted by an electrode pair is provided.

19. The method according to claim 16, wherein the method further comprises actively heating the sensor element and keeping the sensor element at a constant temperature.

20. The method according to claim 16, wherein the method further comprises providing a further sensor element, configured substantially identical to the at least one sensor element, in the exhaust gas system preceding the catalyzer unit and using the second sensor element for measuring nitrogen monoxide concentration in the exhaust gas.

* * * * *